(12) United States Patent
Park (10) Patent No.: US 9,862,749 B2
(45) Date of Patent: Jan. 9, 2018

(54) ANALOGUE PEPTIDE CMA3 DERIVED FROM CM-MA PEPTIDE AND USE THEREOF

(71) Applicant: Industry-Academic Cooperation Foundation, Chosun University, Gwangju (KR)

(72) Inventor: Yoonkyung Park, Nam-myeon (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 0 days.

(21) Appl. No.: 15/112,118

(22) PCT Filed: Jan. 14, 2015

(86) PCT No.: PCT/KR2015/000386
§ 371 (c)(1),
(2) Date: Jul. 15, 2016

(87) PCT Pub. No.: WO2015/108333
PCT Pub. Date: Jul. 23, 2015

(65) Prior Publication Data
US 2016/0326218 A1    Nov. 10, 2016

(30) Foreign Application Priority Data

Jan. 17, 2014 (KR) ........................ 10-2014-0005936

(51) Int. Cl.
| | | |
|---|---|---|
| C07K 14/00 | (2006.01) | |
| C07K 14/435 | (2006.01) | |
| C07K 14/46 | (2006.01) | |
| A61K 8/64 | (2006.01) | |
| A61Q 19/00 | (2006.01) | |
| A61Q 19/10 | (2006.01) | |
| A61K 38/00 | (2006.01) | |

(52) U.S. Cl.
CPC ............... *C07K 14/00* (2013.01); *A61K 8/64* (2013.01); *A61Q 19/00* (2013.01); *A61Q 19/10* (2013.01); *C07K 14/43563* (2013.01); *C07K 14/463* (2013.01); *A61K 38/00* (2013.01); *C07K 2319/00* (2013.01)

(58) Field of Classification Search
CPC .................................................... C07K 14/00
See application file for complete search history.

(56) References Cited

U.S. PATENT DOCUMENTS

| | | | |
|---|---|---|---|
| 6,800,727 B2 | 10/2004 | Hahm et al. | |
| 2010/0310644 A1* | 12/2010 | Liebmann | ................ A61K 8/64 424/450 |

FOREIGN PATENT DOCUMENTS

| | | |
|---|---|---|
| KR | 10-1999-031002 | 5/1999 |
| KR | 10-2003-024961 | 3/2003 |
| KR | 10-2012-138432 | 12/2012 |
| KR | 10-2013-078561 | 7/2013 |
| KR | 10-2013-107985 | 10/2013 |

OTHER PUBLICATIONS

Shin et al., 1999, Structure-antibacterial, antitumor and hemolytic activity relationships of cecropin A-magainin 2 and cecropin A-melittin hybrid peptides, J Peptide Res, 53: 82-90.*
Search Report, dated Apr. 7, 2015, corresponding to International Application No. PCT/KR2015/000386 (filed Jan. 14, 2015), parent of the present application, 7 pp.

* cited by examiner

*Primary Examiner* — Amber D Steele
(74) *Attorney, Agent, or Firm* — Lathrop & Gage LLP

(57) ABSTRACT

The present invention relates to a novel analogue antibiotic peptide derived from a CM-MA peptide and a use thereof. Specifically, the novel antibiotic peptides represented by SEQ. ID. NO: 2 to SEQ. ID. NO: 7 (CAM 1 to CMA 6) were synthesized by using a CM-MA antibiotic peptide, in which amphiphilic cecropin A (CA) and magainin 2 (MA) are conjugated, as a template. The synthesized antibiotic peptide exhibits antibiotic activity on gram-positive bacteria and gram-negative bacteria and low cytotoxicity on human red blood cells and human normal cell lines (HaCaT), and thus the antibiotic peptide of the present invention can be favorably used as an active ingredient of an antibiotic agent, a cosmetic composition, a food additive, a feed additive, and a biological pesticide.

13 Claims, 3 Drawing Sheets

SEQUENCE LISTING

```
<160> NUMBER OF SEQ ID NOS: 7

<210> SEQ ID NO 1
<211> LENGTH: 20
<212> TYPE: PRT
<213> ORGANISM: Artificial
<220> FEATURE:
<223> OTHER INFORMATION: CA-MA Sequence

<400> SEQUENCE: 1

Lys Trp Lys Leu Phe Lys Lys Ile Gly Ile Gly Lys Phe Leu His Ser
1               5                   10                  15

Ala Lys Lys Phe
            20

<210> SEQ ID NO 2
<211> LENGTH: 20
<212> TYPE: PRT
<213> ORGANISM: Artificial
<220> FEATURE:
<223> OTHER INFORMATION: CMA1 Sequence

<400> SEQUENCE: 2

Lys Trp Lys Leu Phe Lys Lys Ile Gly Ile Gly Lys His Phe Leu Ser
1               5                   10                  15

Ala Lys Lys Phe
            20

<210> SEQ ID NO 3
<211> LENGTH: 20
<212> TYPE: PRT
```

<213> ORGANISM: Artificial
<220> FEATURE:
<223> OTHER INFORMATION: CMA2 Sequence

<400> SEQUENCE: 3

Lys Trp Lys Leu Phe Lys Lys Ile Gly Ile Gly Lys Phe Leu Ser Ala
1               5                   10                  15

His Lys Lys Phe
            20

<210> SEQ ID NO 4
<211> LENGTH: 20
<212> TYPE: PRT
<213> ORGANISM: Artificial
<220> FEATURE:
<223> OTHER INFORMATION: CMA3 Sequence

<400> SEQUENCE: 4

Lys Trp Lys Leu Lys Lys His Ile Gly Ile Gly Lys His Phe Leu Ser
1               5                   10                  15

Ala Lys Lys Phe
            20

<210> SEQ ID NO 5
<211> LENGTH: 20
<212> TYPE: PRT
<213> ORGANISM: Artificial
<220> FEATURE:
<223> OTHER INFORMATION: CMA4 Sequence

<400> SEQUENCE: 5

Lys Trp Lys His Leu Lys Lys Ile Gly Ile Gly Lys Phe Leu Ser Ala
1               5                   10                  15

His Lys Lys Phe
            20

<210> SEQ ID NO 6
<211> LENGTH: 20
<212> TYPE: PRT
<213> ORGANISM: Artificial
<220> FEATURE:
<223> OTHER INFORMATION: CMA5 Sequence

<400> SEQUENCE: 6

Lys Trp Lys His Leu Lys Lys Ile Gly Ile Gly Lys His Phe Leu Ser
1               5                   10                  15

Ala Lys Lys Phe
            20

<210> SEQ ID NO 7
<211> LENGTH: 20
<212> TYPE: PRT
<213> ORGANISM: Artificial
<220> FEATURE:
<223> OTHER INFORMATION: CMA6 Sequence

<400> SEQUENCE: 7

Lys Trp Lys Leu Phe Lys Lys Ile Gly Ile Gly Lys Phe Leu Gln Ser
1               5                   10                  15

Ala Lys Lys Phe
            20

ANALOGUE PEPTIDE CMA3 DERIVED FROM CM-MA PEPTIDE AND USE THEREOF

CROSS-REFERENCE TO RELATED APPLICATIONS

This application is a U.S. National Stage Application filed under 35 U.S.C. §371 of International Application No. PCT/KR2015/000386, filed Jan. 14, 2015, which claims the benefit of Korean Application No. KR 10-2014-0005936, filed Jan. 17, 2014. Both of these applications are hereby incorporated by reference in their entireties.

BACKGROUND OF THE INVENTION

1. Field of the Invention

The present invention relates to a novel analogue antibiotic peptide derived from a CM-MA peptide and a use thereof.

2. Description of the Related Art

Bacterial infection is the most common and general but sometimes an incurable cause of disease. Unfortunately, bacteria gain resistance against antibiotics owing to the over-use of antibiotics. In fact, gaining resistance of bacteria against a new antibiotic agent outruns the development of a new antibiotic analogue. For example, lethal bacteria such as *Enterococcus faecalis, Mycobacterium tuberculosis,* and *Pseudomonas aeruginosa* have grown their resistance against almost all antibiotics known so far (Stuart B. Levy, Scientific American, 1998, 46-53).

Tolerance against antibiotics is different from resistance against antibiotics. Tolerance was first identified in *Pneumococcus* sp. in 1970s and provided an important clue for the mechanism of penicillin (Tomasz et al., Nature, 1970, 227, 138-140). Bacteria that show tolerance stop their growth in the presence of antibiotics but are not dead. Tolerance is generated when the autolytic enzymes such as autolysin are not activated because of the antibiotics inhibiting the enzyme involved in the synthesis of cell wall. This phenomenon explains that penicillin activates endogenous hydrolytic enzyme so as to kill bacteria and reversely bacteria inhibit the activity of the enzyme so as to survive in the presence of antibiotics.

It is a clinically very important fact that bacteria have tolerance against various antibiotics. If it is not possible to kill resistant bacteria, the treatment effect of an antibiotic agent for clinical infection would be diminished (Handwerger and Tomasz, Rev. Infec. Dis., 1985, 7, 368-386). Being tolerant is the first step of being resistant. So, after all the treatment with antibiotics, there are still strains survived. Such strains acquire a new genetic element that shows resistance against antibiotics so that they keep growing in the presence of the antibiotics. Actually all the strains showing resistance are confirmed to have tolerance as well (Liu and Tomasz, J. Infect. Dis., 1985, 152, 365-372). Therefore, it is required to develop a novel antibiotic agent that can kill the strain displaying resistance against antibiotics.

Tolerance is acquired by two different pathways at large in the aspect of mechanism. Phenotypic tolerance is the one that is generated in all of bacteria when the growth rate decreases (Tuomanen E., Revs. Infect. Dis., 1986, 3, S279-S291) and genetic tolerance is the other that is generated by genetic mutation and identified only in some specific bacteria. The basic phenomenon of the two types of tolerance is down regulation of autolysin activity. The down regulation of autolysin activity caused by phenotypic tolerance is temporary but the down regulation of autolysin activity caused by genetic tolerance is permanent because of the mutation that changes the pathway to regulate cell lysis. The simplest genetic tolerance is the defect in autolysin. The deficiency of autolysin did not produce such a strain that had tolerance by some unknown reasons and rather clinical tolerance was observed in the regulation of autolysin (Tuomanen et al., J. infect. Dis., 1988, 158, 36-43).

As explained hereinbefore, it is necessary to develop a novel antibiotic agent in order to cope such bacteria that show resistance against antibiotics. It is more important to develop a novel antibiotic agent that works independently from the autolysin activity. It is thus required to provide a novel antibiotic agent for the treatment of bacterial infection and inflammation.

Bacteria can kill neighbor bacteria by synthesizing peptides or small organic molecules, which are called bacteriocin. The bacteriocin is classified into three groups according to the structure; lantibiotics, nonlantibiotics, and those secreted by signal peptide (Cintas et al., J. Bad., 1998, 180, 1988-1994). Insects and animals can produce endogenous peptide antibiotics (Bevins et al., Ann. Rev. Biochem., 1990, 59, 395-414), which are also divided into three groups according to the structure. The first group is cysteine-rich β-sheet peptides, the second group is α-helical amphiphilic molecules, and the third group is proline-rich peptides (Mayasaki et al., Int. J. Antimicrob. Agents, 1998, 9, 269-280). These antibiotic peptides play an important role in host defense and innate immune system (Boman, H. G., Cell, 1991, 65, 205; Boman, H. G., Annu. Rev. Microbiol., 1995, 13, 61). These anti-bacterial peptides display different structures generated by different amino acid sequences. The most frequently observed antibacterial peptide has the cysteine free amphiphilic α-helical structure like cecropin, identified mostly in insects.

The antibacterial activity of the amphiphilic peptide has been most studied among those peptides, based on which attempts have been made to develop an antibacterial agent. The amphiphilic peptides reported so far are magainin 2 (MA), cecropin A (CA), and melittin (ME), etc.

The cecropin family amphiphilic peptide was first identified in drosophila. Later, it was also found in silkworm pupa and hog small intestine. Cecropin A exhibits high antibacterial activity but weak anti-fungal activity and anti-cancer activity (Boman, H. G. and Hultmark, D., Annu. Rev. Microbiol., 1987, 41, 103). Magainin 2 peptide has no cytotoxicity and displays anti-fungal, anticancer, and anti-protozoan activities along with anti-bacterial activity (Zasloff, M., Proc. Natl. Acad. Sci. USA, 1987, 84, 5449). It is also known that a synthetic peptide having an excellent anti-bacterial, anti-fungal, or anti-cancer activity can be prepared as a conjugation peptide produced by conjugating some parts of sequences of the two peptides above (Chan, H. C., et al., FEBS Lett., 1989, 259, 103; Wade, D., et al., Int. J. Pept. Prot. Res., 1992, 40, 429).

The present inventors tried to produce a novel synthetic peptide with the improved antibacterial activity from the conventional peptides reported to have an antibacterial activity. As a result, the inventors succeeded in synthesizing the novel antibiotic peptides represented by SEQ. ID. NO: 2~NO: 7 (CMA1~CMA 6) by using a CA-MA antibiotic peptide, in which amphiphilic cecropin A (CA) and magainin 2 (MA) were conjugated, as a template. The synthesized antibiotic peptides displayed antibacterial activity against gram-positive and gram negative bacteria and at the same time displayed low cytotoxicity to human red blood cells and human normal cell lines (HaCaT). Therefore, the synthesized novel antibiotic peptides were confirmed to be effectively used as an active ingredient of an antibiotic agent, a cosmetic composition, a food additive, a feed additive, a biological pesticide, and a quasi-drug, leading to the completion of the present invention.

SUMMARY OF THE INVENTION

It is an object of the present invention to provide a novel antibiotic peptide having excellent antibacterial activity but low cytotoxicity, produced from a CA-MA antibiotic peptide in which amphiphilic cecropin A (CA) and magainin 2 (MA) are conjugated.

To achieve the above object, the present invention provides an antibiotic peptide composed of the amino acid sequence represented by SEQ. ID. NO: 1 having one of the following mutations of i)~v) in the sequence:

i) substitution of the $4^{th}$ amino acid residue with histidine;
ii) substitution of the $5^{th}$ amino acid residue with lysine or leucine;
iii) substitution of the $7^{th}$ amino acid residue with histidine;
iv) change in the order of the amino acid residues ranging from the $13^{th}$ residue to the $17^{th}$ residue, and substitution of one of those amino acid residues with histidine; and
v) substitution of the $15^{th}$ amino acid residue with glutamine.

The present invention also provides an antibiotic agent comprising the antibiotic peptide above as an active ingredient.

The present invention also provides a cosmetic composition comprising the antibiotic peptide above as an active ingredient.

The present invention also provides a food additive comprising the antibiotic peptide above as an active ingredient.

The present invention also provides a feed additive comprising the antibiotic peptide above as an active ingredient.

The present invention also provides a biological pesticide comprising the antibiotic peptide above as an active ingredient.

The present invention also provides an antimicrobial quasi-drug composition comprising the antibiotic peptide above as an active ingredient.

The present invention further provides an antimicrobial method in a subject containing the step of administering an effective dose of the antibiotic peptide above to the subject.

The present invention further provides a use of the antibiotic peptide for the preparation of an antibiotic agent.

The present invention also provides a use of the antibiotic peptide for the preparation of a cosmetic composition.

The present invention also provides a use of the antibiotic peptide for the preparation of a food additive.

The present invention also provides a use of the antibiotic peptide for the preparation of a feed additive. The present invention also provides a use of the antibiotic peptide for the preparation of a biological pesticide.

In addition, the present invention provides a use of the antibiotic peptide for the preparation of an antimicrobial quasi-drug composition.

Advantageous Effect

The antibiotic peptides comprising the amino acid sequences represented by SEQ. ID. NO: 2~NO: 7, produced from a CM-MA antibiotic peptide in which amphiphilic cecropin A (CA) and magainin 2 (MA) are conjugated, display excellent antimicrobial activity against both gram positive and gram negative bacteria and exhibit low cytotoxicity to human red blood cell and human normal cell lines, so that the antibiotic peptide of the present invention can be effectively used as an active ingredient of an antibiotic agent, a cosmetic composition, a food additive, a feed additive, and a biological pesticide.

BRIEF DESCRIPTION OF THE DRAWINGS

The application of the preferred embodiments of the present invention is best understood with reference to the accompanying drawings, wherein:

■: CMA1, □: CMA2, ▲: CMA3, Δ: CMA4, ●: CMA5, and ○: CMA6;

FIG. 1A displays the formation of the secondary structure in the peptides above in 10 mM sodium phosphate solution; and FIG. 1B displays the formation of the secondary structure in the peptides above in 30 mM sodium dodecyl sulfate solution

DESCRIPTION OF THE PREFERRED EMBODIMENTS

Hereinafter, the present invention is described in detail.

The present invention provides an antibiotic peptide composed of the amino acid sequence represented by SEQ. ID. NO: 1 having one of the following mutations of i)~v) in the sequence:

i) substitution of the $4^{th}$ amino acid residue with histidine;
ii) substitution of the $5^{th}$ amino acid residue with lysine or leucine;
iii) substitution of the $7^{th}$ amino acid residue with histidine;
iv) change in the order of the amino acid residues ranging from the $13^{th}$ residue to the $17^{th}$ residue, and substitution of one of those amino acid residues with histidine; and
v) substitution of the $15^{th}$ amino acid residue with glutamine.

The peptide comprising the amino acid sequence represented by SEQ. ID. NO: 1 is the CM-MA antibiotic peptide, in which amphiphilic cecropin A (CA) and magainin 2 (MA) are conjugated.

The antibiotic peptide above is preferably the peptide comprising one of the amino acid sequences represented by SEQ. ID. NO: 2~NO: 7, but not always limited thereto. The substitution herein plays a role of lowering cytotoxicity by increasing or decreasing electrodes and of increasing or at least maintaining antibacterial activity against gram negative and gram positive bacteria.

The method for the synthesis is preferably the conventional chemical synthesis method accepted in this field (W. H. Freeman and Co., Proteins; structures and molecular principles, 1983), and more precisely solution phase peptide synthesis, solid-phase peptide synthesis, fragment condensation, and F-moc or T-BOC chemical method is preferred, and most preferably solution phase peptide synthesis method (Merrifield, R B., J. Am. Chem. Soc., 85, 2149, 196) is used, but not always limited thereto.

The antibiotic peptide herein preferably displays the antibacterial activity against gram negative or gram positive bacteria, but not always limited thereto.

The gram negative bacteria herein preferably include all the gram negative microorganisms notified to those in the art, which are exemplified by *Escherichia* sp., *Pseudomonas* sp., *Salmonella* sp., *Leptospira* sp., and *Richettsia* sp. More precisely, the gram negative microorganism is one or more microorganisms selected from the group consisting of *Escherichia* sp., *Pseudomonas* sp., and *Salmonella* sp., and most preferably the gram negative microorganism herein is one or more microorganisms selected from the group consisting of *Escherichia coli, Pseudomonas aeruginosa*, and *Salmonella typhimurium*, but not always limited thereto.

The gram positive bacteria herein preferably include all the gram positive microorganisms notified to those in the art, which are exemplified by *Staphylococcus* sp., *Listeria* sp., *Staphylococcus* sp., *Corynebacterium* sp., *Lactobacillus* sp, and *Bacillus* sp. More precisely, the gram positive microorganism is one or more microorganisms selected from the group consisting of *Staphylococcus* sp., *Listeria* sp., and *Staphylococcus* sp., and most preferably the gram positive microorganism herein is one or more microorganisms selected from the group consisting of *Staphylococcus aureus, Listeria monocytogenes*, and *Staphylococcus epidermidis*, but not always limited thereto.

The antibiotic peptide above preferably displays a low cytotoxicity to human derived cells, but not always limited thereto.

In a preferred embodiment of the present invention, the present inventors conjugated the amphiphilic cecropin A (CA) with magainin 2 (MA), resulting in the synthesis of the CA-MA antibiotic peptide comprising the amino acid sequence represented by SEQ. ID. NO: 1. By using the peptide as a template, the inventors changed the position of any of the amino acid residues in the sequence ranging from the $13^{th}$ residue to the $17^{th}$ residue at random and then substituted phenylalanine with histidine (CMA1), alanine with histidine (CMA2), and substituted the $5^{th}$ phenylalanine with lysine and the $7^{th}$ lysine with histidine. The inventors changed the position of any of the amino acid residues in the sequence ranging from the $13^{th}$ residue to the $17^{th}$ residue and then substituted phenylalanine with histidine (CMA3), and substituted the $4^{th}$ leucine with histidine and the $5^{th}$ phenylalanine with leucine. The inventors also changed the position of any of the amino acid residues in the sequence ranging from the $13^{th}$ residue to the $_{17}$th residue and then substituted $17^{th}$ alanine with histidine, resulting in the preparation of CMA4. With the substitution of the $13^{th}$ phenylalanine with histidine, CMA5 was prepared. CMA6 was also constructed by substituting the $15^{th}$ amino acid residue histidine of the control CA-MA antibiotic peptide with glutamine. As a result, CAM1~CMA 6 peptides represented by SEQ. ID. NO: 2~NO: 7 were synthesized (see Table 1).

The present inventors investigated whether or not the CA-MA antibiotic peptide synthesized above and the experimental CMA1, CMA2, CMA3, CMA4, CMA5, and CMA6 had the antibacterial activity against gram negative and gram positive bacteria. As a result, it was confirmed that the experimental peptides exhibited similar MIC level to the CA-MA peptide (see Tables 2 and 3).

The present inventors also investigated whether or not the control peptide (CA-MA) and the experimental peptides (CMA1, CMA2, CMA3, CMA4, CMA5, and CMA6) induced hemolysis of human red blood cells (hRBC) and had cytotoxicity to HaCaT. As a result, when the peptides were treated to hRBC and HaCaT at the concentration of 200 μM, hemolysis was not induced by the experimental peptides, compared with the control, and instead the cell survival rate was significantly increased by the experimental peptides. Among the experimental peptides, CMA3 displayed the most excellent effect (see Table 4).

To investigate the secondary structures of the control and the experimental antibiotic peptides, circular dichroism was performed. As a result, it was confirmed that all the peptides exhibited α-helical structure in 30 mM sodium dodecyl sulfate (SDS) solution (see FIG. 1).

The present inventor investigated the antibacterial activity of the antibiotic peptides of the invention more thoroughly. As a result, it was confirmed that the control CM-MA peptide and the experimental CMA3 peptide lied on the *E. coli* cell membrane (see FIG. 2) and made a big hole thereon to exhibit the antibacterial activity (see FIG. 3).

Therefore, the analogue antibiotic peptides (CMA1~CMA 6) derived from the CM-MA peptide of the present invention have a strong antibacterial activity and at the same time display a low cytotoxicity to human derived cells, so that the antibiotic peptides of the invention can be effectively used as an active ingredient of an antibacterial composition.

The present invention also provides an antibiotic agent comprising the antibiotic peptide above as an active ingredient.

The present invention further provides an antimicrobial method in a subject containing the step of administering an effective dose of the antibiotic peptide above to the subject.

The present invention also provides a use of the antibiotic peptide for the preparation of an antibiotic agent.

The peptide comprising the amino acid sequence represented by SEQ. ID. NO: 1 is the CM-MA antibiotic peptide, in which amphiphilic cecropin and magainin are conjugated.

The antibiotic peptide above is preferably the peptide comprising one of the amino acid sequences represented by SEQ. ID. NO: 2~NO: 7, but not always limited thereto. The substitution herein plays a role of lowering cytotoxicity by increasing or decreasing electrodes and of increasing or at least maintaining antibacterial activity against gram negative and gram positive bacteria.

The antibiotic peptide herein preferably displays the antibacterial activity against gram negative or gram positive bacteria, but not always limited thereto.

The gram negative bacteria herein preferably include all the gram negative microorganisms notified to those in the art, which are exemplified by *Escherichia* sp., *Pseudomonas* sp., *Salmonella* sp., *Leptospira* sp., and *Richettsia* sp. More precisely, the gram negative microorganism is one or more microorganisms selected from the group consisting of *Escherichia* sp., *Pseudomonas* sp., and *Salmonella* sp., and most preferably the gram negative microorganism herein is one or more microorganisms selected from the group consisting of *Escherichia coli, Pseudomonas aeruginosa*, and *Salmonella typhimurium*, but not always limited thereto.

The gram positive bacteria herein preferably include all the gram positive microorganisms notified to those in the art, which are exemplified by *Staphylococcus* sp., *Listeria* sp., *Staphylococcus* sp., *Corynebacterium* sp., *Lactobacillus* sp, and *Bacillus* sp. More precisely, the gram positive microorganism is one or more microorganisms selected from the group consisting of *Staphylococcus* sp., *Listeria* sp., and *Straphylococcus* sp., and most preferably the gram positive microorganism herein is one or more microorganisms selected from the group consisting of *Staphylococcus aureus*, *Listeria monocytogenes*, and *Staphylococcus epidermidis*, but not always limited thereto.

The antibiotic peptide above preferably displays a low cytotoxicity to human derived cells, but not always limited thereto.

The analogue antibiotic peptides (CMA1~CMA 6) derived from the CM-MA antibiotic peptide of the present invention have a strong antibacterial activity and at the same time display a low cytotoxicity to human derived cells, so that the antibiotic peptides of the invention can be effectively used as an active ingredient of an antibiotic agent.

The peptide of the present invention can be administered parenterally and be used in general form of pharmaceutical formulation. The parenteral administration indicates the administration via non-oral pathways such as intrarectal, intravenous, intraperitoneal, intramuscular, intraarterial, percutaneous, intranasal, inhale, ophthalmic, and hypodermic administration, etc. When the antibiotic peptide of the invention is treated as a medicine, one or more effective ingredients having the same or similar functions can be included.

The antibiotic peptide of the present invention can be prepared for parenteral administration by mixing with generally used diluents or excipients such as fillers, extenders, binders, wetting agents, disintegrating agents and surfactant. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The antibiotic peptide of the present invention can be mixed with the pharmaceutically acceptable carriers such as saline or organic solvents. To increase the stability or absorptiveness of the peptide, it can also be mixed with carbohydrates such as glucose, sucrose or dextran, antioxidants such as ascorbic acid or glutathione, chelating agents, low-molecular proteins, or other stabilizers.

The effective dose of the antibiotic peptide of the present invention is 1~2 mg/kg and more preferably 0.5~1 mg/kg, which is preferably administered 1~3 times a day.

The effective dose of the antibiotic peptide of the present invention can be administered in the form of bolus, by single dose having relatively short period of infusion or by multiple doses of the fractionated treatment protocol for a long term. The decision of an effective dosage depends on the administration pathway, treatment times, age and other conditions of a patient, etc. Therefore, any expert who has knowledge on this field can decide the effective dosage of the antibiotic peptide of the present invention.

The present invention also provides a cosmetic composition comprising the antibiotic peptide above as an active ingredient.

The present invention also provides a use of the antibiotic peptide for the preparation of a cosmetic composition.

The analogue antibiotic peptides (CMA1~CMA 6) derived from the CM-MA antibiotic peptide of the present invention have a strong antibacterial activity and at the same time display a low cytotoxicity to human derived cells, so that the antibiotic peptides of the invention can be effectively used as an active ingredient of a cosmetic composition.

The cosmetic composition of the present invention can include, in addition to the antibiotic peptide, any conventional ingredients generally used in cosmetics, for example such additives and carriers as stabilizers, solubilizers, vitamins, pigments and flavors.

The concentration of the peptide of the invention in the cosmetic composition of the present invention is preferably 0.1~50 weight % and more preferably 1~10 weight % by the weight of the cosmetic composition.

The cosmetic composition of the present invention can be formulated in any form that can be accepted in the art, which is exemplified by solution, suspension, emulsion, paste, gel, cream, lotion, powder, soap, surfactant-containing cleansing, oil, powdered foundation, emulsified foundation, wax foundation and spray, but not always limited thereto. Particularly, the cosmetic composition of the present invention can be prepared in the form of soft lotion (skin), nutrition lotion (milk lotion), nutrition cream, massage cream, essence, eye cream, cleansing cream, cleansing foam, cleansing water, pack, spray or powder.

In the case that the cosmetic composition is formulated as paste, cream or gel, the proper carrier can be selected from the group consisting of animal oil, vegetable oil, paraffin, starch, tracanth, cellulose derivative, polyethylene glycol, silicon, bentonite, silica, talk and zinc oxide.

In the case that the cosmetic composition is formulated as powder or spray, the proper carrier can be selected from the group consisting of lactose, talc, silica, aluminum hydroxide, calcium silicate and polyamide powder, and in particular if the composition of the present invention is formulated as spray, a propellant such as chlorofluorohydrocarbon, propane/butane or dimethyl ether can be additionally included.

In the case that the cosmetic composition is formulated as liquid or emulsion, the proper carrier can be selected from the group consisting of solvent, solubilizer and emulsifier, which is exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the cosmetic composition is formulated as suspension, the proper carrier can be selected from the group consisting of liquid diluent such as water, ethanol or propylene glycol; suspending agent such as ethoxylated isostearyl alcohol, polyoxyethylene sorbitol ester and polyoxyethylene sorbitan ester; microcrystalline cellulose; aluminum methahydroxide; bentonite; agar; and tragacanth.

In the case that the cosmetic composition is formulated as surfactant-containing cleansing, the proper carrier can be selected from the group consisting of aliphatic alcohol sulfate, aliphatic alcohol ether sulfate, sulfosuccinic monoester, isethionate, imidazolinum derivative, methyltaurate, sarcosinate, fatty acid amide ether sulfate, alkyl amidobetain, aliphatic alcohol, fatty acid glyceride, fatty acid diethanolamide, vegetable oil, lanolin derivative and ethoxylated glycerol fatty acid ester.

The present invention also provides a food additive comprising the antibiotic peptide above as an active ingredient.

The present invention also provides a use of the antibiotic peptide for the preparation of a food additive.

The analogue antibiotic peptides (CMA1~CMA 6) derived from the CM-MA antibiotic peptide of the present invention have a strong antibacterial activity and at the same time display a low cytotoxicity to human derived cells, so that the antibiotic peptides of the invention can be effectively used as an active ingredient of a food additive.

The antibiotic peptide of the present invention can be used as a food additive. In that case, the peptide can be added as it is or as mixed with other food components according to the conventional method. The mixing ratio of active ingredients can be regulated according to the purpose of use. In general, to produce health food or beverages, the antibiotic peptide of the present invention is added preferably by up to 15 weight part and more preferably by up to 10 weight part. However, if long term administration is required, the content can be lower than the above but higher content can be accepted as well since the antibiotic peptide of the present invention has been proved to be very safe.

The food herein is not limited. For example, the antibiotic peptide of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in a wide sense, almost every food applicable in the production of health food can be included.

The present invention also provides a feed additive comprising the antibiotic peptide above as an active ingredient.

The present invention also provides a use of the antibiotic peptide for the preparation of a feed additive.

The analogue antibiotic peptides (CMA1~CMA 6) derived from the CM-MA antibiotic peptide of the present invention have a strong antibacterial activity and at the same time display a low cytotoxicity to human derived cells, so that the antibiotic peptides of the invention can be effectively used as an active ingredient of a feed additive.

The feed composition of the present invention can take the place of the conventional antibiotics and inhibit the growth of a harmful food pathogen, which favors keeping the animal's condition in good shape, and at the same time can increase the quality of meat, the weight of an animal, the production of milk, and immunity of an animal as well. The feed composition of the present invention can be prepared in the forms of fermented feed, formulated feed, pellet, and silage.

The fermented feed herein can be prepared by fermenting an organic material with various microorganisms and enzymes together with the peptide of the invention. The formulated feed can be prepared by mixing various general feeds with the peptide of the invention. The feed in the form of pellet can be prepared by pressing and heating the formulated feed in a pellet machine. The feed in the form of silage can be prepared by fermenting green forage with the microorganism of the present invention. The wet-fermented feed herein can be prepared by the following steps; collecting organic materials such as food waste, sterilizing and mixing the organic materials with an excipient for the regulation of moisture, and fermenting the organic materials at a proper temperature for at least 24 hours to regulate the level of moisture of the mixture to be about 70%. The fermented dry feed herein can be prepared by adding another step of drying the wet-fermented feed above to the above steps of preparing method for the wet-fermented feed to control the moisture level to be about 30~40%.

The present invention also provides an antiseptic composition comprising the antibiotic peptide above as an active ingredient.

The present invention also provides an antimicrobial quasi-drug composition comprising the antibiotic peptide above as an active ingredient.

The present invention also provides an antimicrobial biological pesticide comprising the antibiotic peptide above as an active ingredient.

In addition, the present invention provides a use of the antibiotic peptide for the preparation of an antimicrobial quasi-drug composition.

The analogue antibiotic peptides (CMA1~CMA 6) derived from the CM-MA antibiotic peptide of the present invention have a strong antibacterial activity and at the same time display a low cytotoxicity to human derived cells, so that the antibiotic peptides of the invention can be effectively used as an active ingredient of an antimicrobial biological pesticide, an antiseptic composition, and a quasi-drug composition.

The antiseptic composition herein can be exemplified by a cosmetic preservative or a pharmaceutical preservative. The food preservative, cosmetic preservative, and pharmaceutical preservative can include germicides or antioxidants in order to prevent spoilage, decomposition, discoloration, and chemical change, and can also include functional antibiotics to inhibit the growth of spoilage bacteria or to kill them by inhibiting the growth of such microorganisms as bacteria, fungi, and yeasts. The antiseptic composition herein has to be non-toxic and be effective even with a small amount.

When the composition of the present invention is used as a quasi-drug additive, the extract or fraction of the invention can be added as it is or together with other quasi-drug components according to the conventional method. The ratio of active ingredients can be adjusted according to the purpose of use.

The quasi-drug composition of the present invention can be disinfecting cleanser, shower foam, garglin, wet tissue, laundry detergent, hand wash, humidifier filler, mask, ointment, patch, or filter filler, but not always limited thereto.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Synthesis, Separation, and Purification of Peptide

The present inventors replaced the $4^{th}$ amino acid of the mother peptide comprising the amino acid sequence represented by CA-MA with histidine, the $5^{th}$ amino acid with lysine and leucine, and the $7^{th}$ amino acid with histidine, according to the solution phase peptide synthesis method of Merrifield (Merrifield, R B., J. Am. Chem. Soc., 85, 2149, 196), and also changed the position of any of the amino acid residues in the sequence ranging from the $13^{th}$ residue to the $_{17}$th residue at random, which were then replaced with histidine. The $15^{th}$ amino acid of the antibiotic peptide comprising the amino acid sequence represented by CA-MA was also replaced with glutamine (Table 1).

Particularly, the peptide having the carboxyl terminal in the form of NH2 designed in this invention was synthesized by using Rink Amide MBHA-Resin as a starting material.

The peptide having the carboxyl terminal in the form of OH was synthesized by using Fmoc-amino acid-Wang Resin as a starting material.

Chain extension by Fmoc-amino acid coupling was performed by DCC (N-hydroxybenzo trizole(HOBt)-dicyclohexycarbodiimide) method. Fmoc-amino acid of the amino terminal of each peptide was coupled and then Fmoc group was eliminated by using NMP (20% piperidine/N-methyl pyrolidone) solution, followed by washing with NMP and DCM (dichoromethane) several times. Then, the peptide was dried with nitrogen gas, to which the mixed solution comprising TFA (trifluoroacetic acid), phenol, thioanisole, $H_2O$, and triisopropylsilane at the ratio of 85:5:2.5:2.5 (v/v) was added, followed by reaction for 2~3 hours. Upon completion of the elimination of the protecting group and the separation of the peptide from the resin, the peptide was precipitated by using diethylether and the precipitate was obtained. The obtained crude peptide was purified by reverse-phase (RP) HPLC column (Delta Pak, C18300 Å, 15, 19.0 mm×30 cm, Waters, USA) with acetonitrile gradient containing 0.05% TFA. The synthetic peptide was hydrolyzed with 6 N HCl at 110° C. and the residue was concentrated under reduced pressure. The residue was then dissolved in 0.02 N HCl and the amino acid composition was analyzed by using an amino acid analyzer (Hitachi 8500 A). MALDI mass spectrometry (Hill, et al., Rapid Commun. Mass Spectrometry, 5: 395, 1991) was performed to confirm the purity and the molecular weight of the obtained peptide.

As a result, as shown in Table 1, the peptides comprising the amino acid sequences represented by SEQ. ID. NO: 1~NO: 7 were confirmed to be synthesized with the purity of at least 95% and their molecular weights were as expected (Table 1).

EXAMPLE 2

Measurement of Antibacterial Activity

To compare the antibacterial activities among those peptides prepared by the method of Example 1 of the invention, the inventors measured MIC (minimal inhibitory concentration) of the peptide which is the minimum concentration for staying without being broken.

Particularly, the strains listed in Table 2 were purchased and cultured in each medium composed as instructed until the mid-log phase. The cells were diluted at the density of $5 \times 10^5$ cells/100 µl, which were then inoculated in a micro-titrate plate (Nunc, USA). Then, the CMA1, CMA2, CMA3, CMA4, CMA5, or CMA6 peptide synthesized in Example 1 was ½ fold diluted in each 96 well plate, and then added to the plate, followed by culture at 37° C. for 12 hours. $OD_{620}$ was measured with a micro-titrate plate reader (Merck Elisa reader, Germany) to determine MIC for each strain. As for the control, the mother peptide CM-MA was treated by the same manner as described above and MIC was also determined.

TABLE 2

Strains used in this invention

|  | Strain | Origin | Accession No. |
|---|---|---|---|
| Gram negative | Escherichia coli | ATCC | ATCC 19115 |
|  | Pseudomonas aeruginosa | ATCC | ATCC 15692 |
|  | Salmonella typhimurium | KCTC | KTCC 1926 |
| Gram positive | Staphylococcus aureus | ATCC | ATCC 25923 |
|  | Listeria monocytogenes | ATCC | ATCC 19115 |
|  | Staphylococcus epidermidis | KCTC | KCTC 3096 |

TABLE 1

Sequence, molecular weight, and retention time of the peptide synthesized in this invention

| Peptide | Amino acid sequence | SEQ. ID. NO: | Molecular weight | Retention time |
|---|---|---|---|---|
| CA-MA | KWKLFKKIGIGKFLHSAKKF-NH$_2$ | SEQ. ID. NO: 1 | 2401.0 | 23.6 |
| CMA1 | KWKLFKKIGIGKHFLSAKKF-NH$_2$ | SEQ. ID. NO: 2 | 2402.2 | 20.9 |
| CMA2 | KWKLFKKIGIGKFLSAHKKF-NH$_2$ | SEQ. ID. NO: 3 | 2404.2 | 22.3 |
| CMA3 | KWKLKKHIGIGKHFLSAKKF-NH$_2$ | SEQ. ID. NO: 4 | 2393.2 | 17.8 |
| CMA4 | KWKHLKKIGIGKFLSAHKKF-NH$_2$ | SEQ. ID. NO: 5 | 2390.8 | 79.1 |
| CMA5 | KWKHLKKIGIGKHFLSAKKF-NH$_2$ | SEQ. ID. NO: 6 | 2392.6 | 17.6 |
| CMA6 | KWKLFKKIGIGKFLQSAKKF-NH$_2$ | SEQ. ID. NO: 7 | 2394.3 | 23.9 |

As a result, as shown in Table 3, CMA1, CMA2, CMA3, CMA4, CMA5, and CMA6 peptides exhibited as high antibacterial activity against both gram negative and gram positive bacteria as the control CA-MA (Table 3).

CMA5, or CMA6 displayed no destruction of red blood cell at the concentration of 200 μM. Therefore, the antibiotic peptide of the invention was confirmed to have less cytotoxicity to red blood cells than the mother peptide (Table 4).

TABLE 3

Antibacterial activity of antibiotic peptide against gram negative and gram positive bacteria

| | Minimal inhibitory concentration (μM) | | | | | |
|---|---|---|---|---|---|---|
| | Gram negative | | | Gram positive | | |
| Peptide | Escherichia coli | P. aeruginosa | S. typhimurium | S. aureus | L. monocytogenes | S. epidermidis |
| CA-MA | 2 | 1 | 1 | 8 | 0.5 | 8 |
| CMA1 | 8 | 8 | 1 | 16 | 4 | 32 |
| CMA2 | 2 | 4 | 1 | 32 | 1 | 16 |
| CMA3 | 4 | 8 | 1 | 32 | 2 | 64 |
| CMA4 | 4 | 16 | 1 | 32 | 2 | 32 |
| CMA5 | 8 | 16 | 1 | 32 | 2 | 64 |
| CMA6 | 4 | 4 | 1 | 16 | 1 | 8 |

EXAMPLE 3

Measurement of Hemolytic Activity

To compare the cytotoxicity of each peptide prepared by the method of Example 1 of the invention, the red blood cell hemolytic activity of the synthesized peptide was measured.

Particularly, human red blood cells were diluted in PBS (pH 7.0) at the concentration of 8%. The cells were treated with the peptide prepared in Example 1 (CM-MA, CMA1, CMA2, CMA3, CMA4, CMA5, or CMA6) at the concentration of 12.5, 25.0, 50.0, 100.0, or 200.0 μM/well, followed by reaction at 37° C. for 1 hour. Then, centrifugation was performed at 1,000 g. The hemoglobin content in the supernatant was confirmed by measuring $OD_{414}$. For the investigation of cell destruction levels, the control cells were treated with 1% Triton X-100 (Sigma, USA), followed by reaction at 37° C. for 1 hour. Then, OD of the supernatant was measured. Considering the red blood cell hemolytic activity of Triton X-100 as 100%, the hemolytic activity of each peptide was calculated through the mathematical formula 1 below.

Hemolysis(%)=(*OD A*−*OD B*)/
(*OD C*−*OD B*)×100    [Mathematical Formula 1]

(In the mathematical formula 1,

OD A is the $OD_{414}$ of the reaction solution treated with each peptide;

OD B is the $OD_{414}$ of the reaction solution treated with PBS; and

OD C is the $OD_{414}$ of the reaction solution treated with 1% Triton X-100.)

As a result, as shown in Table 4, when the mother peptide CA-MA was treated to human red blood cells at the concentration of 200 μM, 6% hemolysis was induced. In the meantime, the peptides CMA1, CMA2, CMA3, CMA4,

TABLE 4

Hemolytic activity of antibiotic peptide

| | % red blood cell hemolysis (peptide conc., μM) | | | | |
|---|---|---|---|---|---|
| Peptide | 200 | 100 | 50 | 25 | 12.5 |
| CA-MA | 6 | 2 | 1 | 0 | 0 |
| CMA1 | 0 | 0 | 0 | 0 | 0 |
| CMA2 | 0 | 0 | 0 | 0 | 0 |
| CMA3 | 0 | 0 | 0 | 0 | 0 |
| CMA4 | 0 | 0 | 0 | 0 | 0 |
| CMA5 | 0 | 0 | 0 | 0 | 0 |
| CMA6 | 0 | 0 | 0 | 0 | 0 |

EXAMPLE 4

Cytotoxicity to Normal Cell Line

To investigate the cytotoxicity of each peptide prepared by the method of Example 1 to human keratinocyte cell line (HaCaT cell line, Dr. N E. Fusenig, Heidelberg, Germany) was measured.

Particularly, the HaCaT cell line cultured in DMEM supplemented with 10% FBS (Fetal Bovine Serum) was distributed in a 96-well plate at the density of $3 \times 10^3$ cells/well, followed by culture for 24 hours. The CM-MA, CMA1, CMA2, CMA3, CMA4, CMA5, or CMA6 peptide prepared in Example 1 was treated to each well at the concentration of 12.5, 25.0, 50.0, 100.0, or 200.0 μM/well, followed by reaction in a 5% $CO_2$ incubator for 24 hours. Upon completion of the culture, 20 ul of the reaction solution containing 5 mg/ml MTT (Thiazolyl Blue Tetrazolium Bromide) dissolved in PBS (phosphate buffered saline) was added to each well, followed by reaction for 4 hours. Then, the supernatant was eliminated. MTT crystal formed thereby was dissolved in 200 ul DMSO and wave-length was observed at 560 nm to investigate cell survival rate.

As a result, as shown in Table 5, when the mother peptide CM-MA was treated to the cells at the concentration of 200 μM, HaCaT cells displayed 1.4% survival rate, suggesting that CM-MA peptide displayed a strong cytotoxicity. On the contrary, CMA1, CMA4, and CMA5 peptides exhibited 51.1%, 64.5%, and 78.9% cell survival rates, suggesting that they had a low cytotoxicity. In particular, CMA3 peptide displayed 92.4% cell survival rate at the concentration of 200 μM, indicating that the peptide hardly had cytotoxicity, compared with the control CA-MA peptide (Table 5).

EXAMPLE 5

Measurement of Circular Dichroism Spectrum

To investigate the formation of α-helical structure, the secondary structure, in the peptides prepared by the method of Example 1, circular dichroism was performed.

Particularly, 30 μM of the peptide prepared in Example 1 (CM-MA, CMA1, CMA2, CMA3, CMA4, CMA5, or CMA6) was added to 10 mM sodium phosphate (pH 7.4) or 30 mM sodium dodecyl sulfate (SDS) solution, which was loaded in 0.1 cm path-length cell. The temperature of jasco 810 spectrophotometer was set at 25° C., with which circular dichroism was performed. The formation of α-helical structure was calculated from the circular dichroism spectrum by using the mathematical formula 2 below.

$$[\theta] = \frac{\theta_{obs}}{10 \cdot l \cdot c}$$ [Mathematical Formula 2]

(In the mathematical formula 2,

θobs indicates the milidegrees of signal;

l indicates the size of cell (cm) presented as the optical path-length; and c indicates the concentration of the peptide (mol/l).

Figure 1:
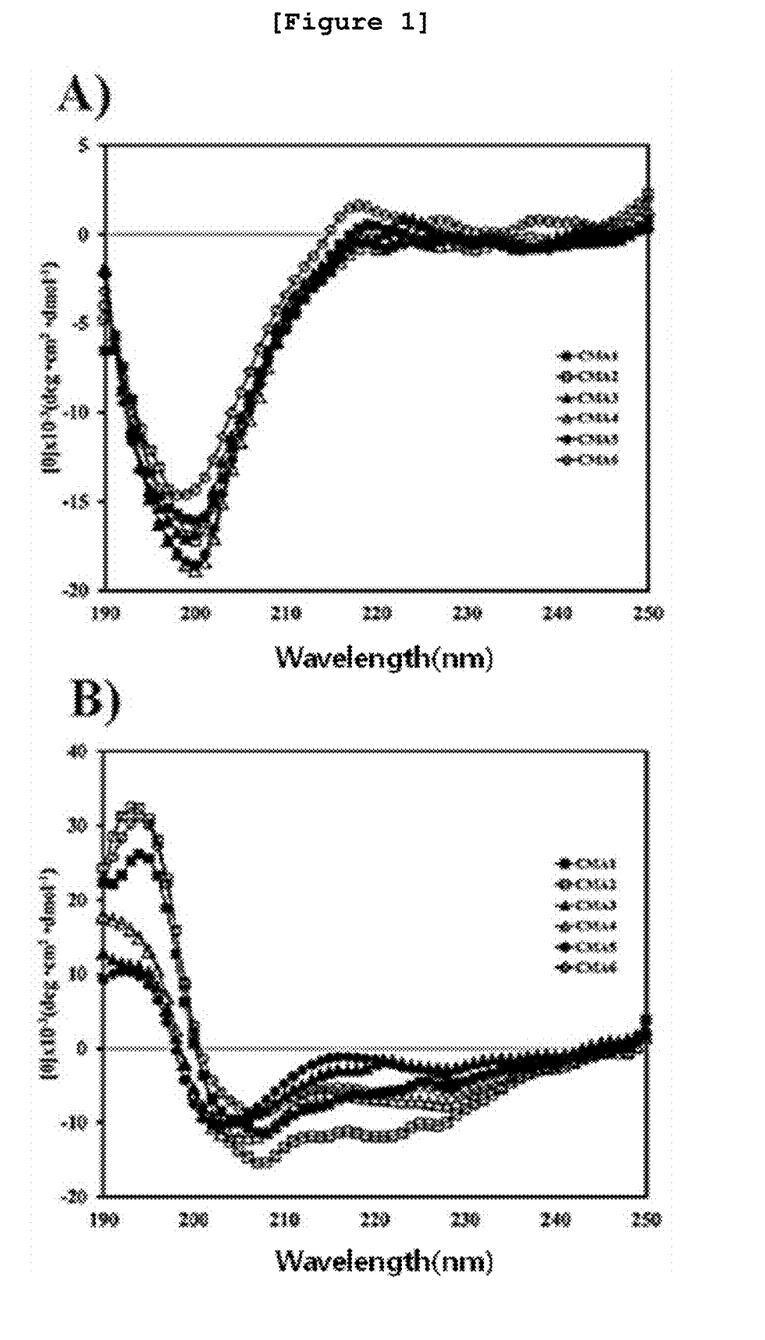
FIG. 1 is a set of diagrams illustrating the formation of the secondary structure in the control antibiotic peptide CA-MA and the experimental antibiotic peptides CMA1, CMA2, CMA3, CMA4, CMA5, and CMA6.

As a result, as shown in FIG. 1, when the peptide was added to 10 mM sodium phosphate solution, the secondary structure was not formed. In the meantime, when the peptide was added to 30 mM SDS solution, all the peptides formed α-helical structure, the secondary structure, even though the degrees were different. Therefore, it was confirmed that the antibiotic peptides of the present invention formed α-helical structure on SDS similar to bacterial membrane (FIG. 1).

EXAMPLE 6

Observation Under Confocal Microscope

To investigate the effect of the peptide prepared by the method of Example 1 on *E. coli* membrane, tetramethylrhodamine (TAMRA) was attached to NH of the C-terminal of the CMA3 peptide selected due to the high antibacterial activity as well as low toxicity even at a higher concentration. Then, the peptide was observed under confocal microscope.

Particularly, TAMRA was attached to NH of the C-terminal of the CA-MA or CMA3 prepared in Example 1, followed by separation. The peptide was treated to *E. coli* at the concentration of ½ the MIC, followed by reaction at 37° C. for 10 minutes. Upon completion of the reaction, pure *E. coli* cells were obtained by centrifugation (4,000 rpm) and the supernatant was eliminated. Then, 50 μl of PBS was added thereto to avoid cell aggregation. The location of the peptide on *E. coli* membrane was investigated by observing under LSM510 confocal microscope.

Figure 2:
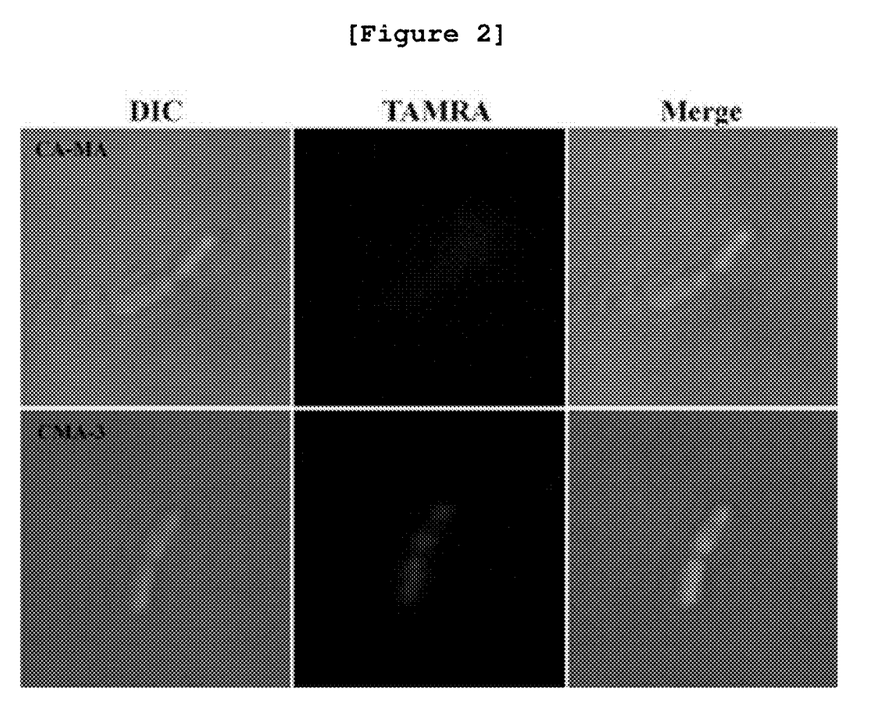
FIG. 2 is a diagram illustrating the effect of TAMRA conjugated to C-terminal of the control antibiotic peptide CA-MA and the experimental antibiotic peptide CMA3 on *E. coli*.

As a result, as shown in FIG. 2, the TAMRA conjugated CMA3 and CM-MA peptides were observed on *E. coli* membrane (FIG. 2).

EXAMPLE 7

Effect of the Antibiotic Peptide on *E. coli*

To investigate precisely the antibacterial activity of the peptide synthesized in this invention, the lysis of *E. coli* membrane by CMA3 was observed by scanning electron microscopy (SEM).

Particularly, *E. coli* was cultured in LB medium (1% bacto-trypton, 0.5% bacto-yeast extract, 1% sodium chloride) until the mid-log phase, which was then diluted in 10 mM Na-phosphate buffer containing 100 mM NaCl at the density of $10^8$ cells/ml. CMA3 or the comparative control CA-MA peptide prepared in Example 1 was treated thereto at the concentration of ½ the MIC, followed by reaction at 37° C. for 10 minutes. Then, 5% glutaraldehyde was treated thereto, followed by fixing at 4° C. for 2 hours. The cells were washed with buffer and dehydrated stepwise by using ethanol. After hydration, critical point dry was performed, followed by golden coating. The cells were observed by scanning electron microscopy (SEM).

Figure 3:
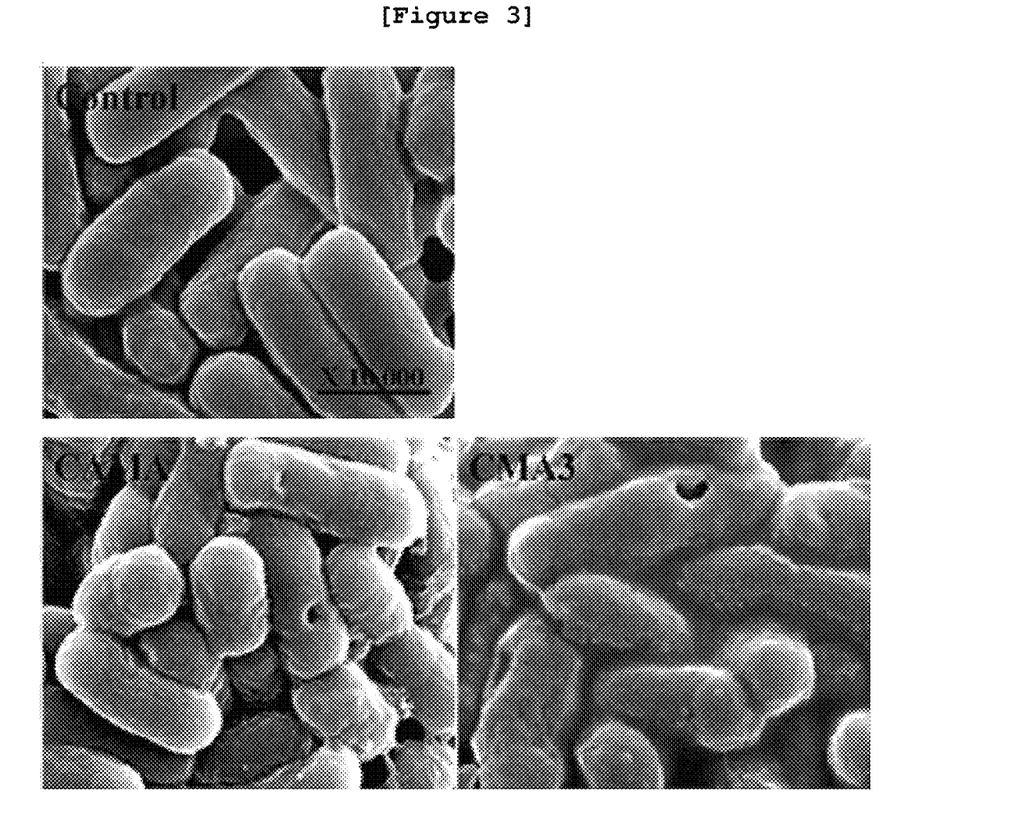
FIG. 3 is a diagram illustrating the destruction of the *E. coli* membrane by the control antibiotic peptide CA-MA and the experimental antibiotic peptide CMA3.

As a result, as shown in FIG. 3, similarly to the result of the treatment of CA-MA to *E. coli*, CMA3 made a hole on the *E. coli* membrane to destroy the membrane, suggesting that the peptide had an effective antibacterial activity (FIG. 3).

The Manufacturing Examples of the composition for the present invention are described hereinafter.

MANUFACTURING EXAMPLE 1

Preparation of Pharmaceutical Formulations

<1-1> Preparation of Powders

| Peptide of the invention | 20 mg |
|---|---|
| Lactose | 20 mg |

Powders were prepared by mixing all the above components, which were filled in airtight packs according to the conventional method for preparing powders.

<1-2> Preparation of Tablets

| Peptide of the invention | 10 mg |
|---|---|
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| Peptide of the invention | 10 mg |
|---|---|
| Crystalline cellulose | 3 mg |
| Lactose | 14.8 mg |
| Magnesium stearate | 0.2 mg |

Capsules were prepared by mixing all the above components, which were filled in gelatin capsules according to the conventional method for preparing capsules.

<1-4> Preparation of Liquid Formulations

| | |
|---|---|
| Peptide of the invention | 20 mg |
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

<1-5> Preparation of Injectable Solutions

| | |
|---|---|
| Peptide of the invention | 10 μg/ml |
| Weak HCl BP | until pH 7.6 |
| Injectable NaCl BP | up to 1 ml |

The peptide of the present invention was dissolved in proper volume of injectable NaCl BP. pH of the prepared solution was regulated as 7.6 by using weak HCl BP. The volume was adjusted by using injectable NaCl BP. The solution was well mixed and filled in 5 ml type I transparent glass ampoules. The ampoules were sealed by melting the glass of opening, followed by autoclave at 120° C. for at least 15 minutes for sterilization.

MANUFACTURING EXAMPLE 2

Preparation of Cosmetics

<2-1> Skin

Antibacterial skin comprising the peptide of the present invention was prepared according to the composition shown in Table 5.

TABLE 5

| Composition | Content (weight %) |
|---|---|
| Peptide of the invention | 0.1~30% |
| 1,3-butyleneglycol | 3.0 |
| Glycerin | 5.0 |
| Polyoxyethylene(60) hydrogenated caster oil | 0.2 |
| Ethanol | 8.0 |
| Citric acid | 0.02 |
| Sodium citrate | 0.06 |
| Antiseptic | Small amount |
| Flavor | Small amount |
| Purified water | To 100 |

<2-2> Lotion

Antibacterial lotion comprising the peptide of the present invention was prepared according to the composition shown in Table 6.

TABLE 6

| Composition | Content (weight %) |
|---|---|
| Peptide of the invention | 0.1~30% |
| 1,3-butyleneglycol | 8.0 |
| Glycerin | 5.0 |
| Squalan | 10.0 |
| Polyoxyethylenesorbitanmonooleate | 2.0 |
| Guaiac wood oil | 0.1~30% |
| 1,3-butyleneglycol | 3.0 |

TABLE 6-continued

| Composition | Content (weight %) |
|---|---|
| Glycerin | 5.0 |
| Polyoxyethylene(60) hydrogenated caster oil | 0.2 |
| Ethanol | 8.0 |
| Citric acid | 0.02 |
| Sodium citrate | 0.06 |
| Antiseptic | Small amount |
| Flavor | Small amount |
| Purified water | To 100 |

<2-3> Essence

Antibacterial essence comprising the peptide of the present invention was prepared according to the composition shown in Table 7.

TABLE 7

| Composition | Content (weight %) |
|---|---|
| Peptide of the invention | 0.1~30% |
| Sitosterol | 1.7 |
| Polyglyceryl-2-olate | 1.5 |
| Ceramide | 0.7 |
| Ceteareth-4 | 1.2 |
| Cholesterol | 1.5 |
| Dicetylphosphate | 0.4 |
| Conc. glycerin | 5.0 |
| Carboxyvinylpolymer | 0.2 |
| Xanthan gum | 0.2 |
| Antiseptic | Small amount |
| Flavor | Small amount |
| Purified water | To 100 |

<2-4> Face Wash (Cleansing Foam)

Antibacterial face wash (cleansing foam) comprising the peptide of the present invention was prepared according to the composition shown in Table 8.

TABLE 8

| Composition | Content (weight %) |
|---|---|
| Peptide of the invention | 0.1~30% |
| N-sodium acylglutamate | 20.0 |
| Glycerin | 10.0 |
| PEG-400 | 15.0 |
| Propyleneglycol | 10.0 |
| POE(15) oleyl alcohol ether | 3.0 |
| Laurin derivative | 2.0 |
| Methylparabene | 0.2 |
| EDTA-4Na | 0.03 |
| Flavor | 0.2 |
| Purified water | To 100 |

<2-5> Nourishing Cream

Antibacterial nourishing cream comprising the peptide of the present invention was prepared according to the composition shown in Table 9.

TABLE 9

| Composition | Content (weight %) |
|---|---|
| Peptide of the invention | 0.1~30% |
| Vaseline | 7.0 |
| Liquid paraffin | 10.0 |
| Beeswax | 2.0 |
| Polysorbate 60 | 2.5 |
| Sorbitan sesquioleate | 1.5 |
| Squalan | 3.0 |
| Propyleneglycol | 6.0 |

TABLE 9-continued

| Composition | Content (weight %) |
|---|---|
| Glycerin | 4.0 |
| Triethanolamine | 0.5 |
| Xanthan gum | 0.5 |
| Tocopheryl acetate | 0.1 |
| Flavor, antiseptic | Small amount |
| Purified water | To 100 |

<2-6> Massage Cream

Antibacterial massage cream comprising the peptide of the present invention was prepared according to the composition shown in Table 10.

TABLE 10

| Composition | Content (weight %) |
|---|---|
| Peptide of the invention | 0.1~30% |
| Propyleneglycol | 6.0 |
| Glycerin | 4.0 |
| Triethanolamine | 0.5 |
| Beeswax | 2.0 |
| Tocopheryl acetate | 0.1 |
| Polysorbate 60 | 3.0 |
| Sorbitan sesquioleate | 2.5 |
| Cetearyl alcohol | 2.0 |
| Liquid paraffin | 30.0 |
| Xanthan gum | 0.5 |
| Flavor, antiseptic | Small amount |
| Purified water | To 100 |

<2-7> Pack

Antibacterial pack comprising the peptide of the present invention was prepared according to the composition shown in Table 11.

TABLE 11

| Composition | Content (weight %) |
|---|---|
| Peptide of the invention | 0.1~30% |
| Propyleneglycol | 2.0 |
| Glycerin | 4.0 |
| Polyvinyl alcohol | 10.0 |
| Ethanol | 7.0 |
| PEG-40 hydrogenated caster oil | 0.8 |
| Triethanolamine | 0.3 |
| Flavor, antiseptic | Small amount |
| Purified water | To 100 |

INDUSTRIAL APPLICABILITY

The antibiotic peptide of the present invention exhibit excellent antibacterial activity but low cytotoxicity to human cells, so that it can be effectively used as an active ingredient of an antibiotic agent, a cosmetic composition, a food additive, a feed additive, and a biological pesticide.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. An antibiotic peptide comprising the amino acid sequence represented by SEQ. ID. NO: 1 having at least one of the following mutations of i)-v) in the sequence:
   i) substitution of the 4$^{th}$ amino acid residue with histidine;
   ii) substitution of the 5$^{th}$ amino acid residue with lysine or leucine;
   iii) substitution of the 7$^{th}$ amino acid residue with histidine;
   iv) change in the order of the amino acid residues ranging from the 13$^{th}$ residue to the 17$^{th}$ residue, and substitution of one of those amino acid residues with histidine; and
   v) substitution of the 15$^{th}$ amino acid residue with glutamine.

2. The antibiotic peptide according to claim 1, wherein the antibiotic peptide comprises one of the amino acid sequences represented by SEQ ID NOs: 2-7.

3. The antibiotic peptide according to claim 1, wherein the antibiotic peptide has the antibacterial activity against gram negative or gram positive microorganism.

4. The antibiotic peptide according to claim 3, wherein the gram negative microorganism is one or more microorganisms selected from the group consisting of *Escherichia coli*, *Pseudomonas aeruginosa*, and *Salmonella typhimurium*.

5. The antibiotic peptide according to claim 3, wherein the gram positive microorganism is one or more microorganisms selected from the group consisting of *Staphylococcus aureus*, *Listeria monocytogenes*, and *Staphylococcus epidermidis*.

6. The antibiotic peptide according to claim 1, wherein the antibiotic peptide exhibits low cytotoxicity to human derived cells.

7. An antibiotic agent comprising the antibiotic peptide of claim 1 as an active ingredient.

8. A cosmetic composition comprising the antibiotic peptide of claim 1 as an active ingredient.

9. A food additive comprising the antibiotic peptide of claim 1 as an active ingredient.

10. A feed additive comprising the antibiotic peptide of claim 1 as an active ingredient.

11. An antimicrobial biological pesticide comprising the antibiotic peptide of claim 1 as an active ingredient.

12. An antimicrobial quasi-drug composition comprising the antibiotic peptide of claim 1 as an active ingredient.

13. An antimicrobial method in a subject containing the step of administering an effective dose of the antibiotic peptide of claim 1 to the subject.

* * * * *